US 11,207,437 B2

(12) United States Patent
Faterioun et al.

(10) Patent No.: US 11,207,437 B2
(45) Date of Patent: Dec. 28, 2021

(54) SEALED HEATER ENGINE FOR A WAX WARMER

(71) Applicant: S. C. Johnson & Son, Inc., Racine, WI (US)

(72) Inventors: Kamran Faterioun, New Berlin, WI (US); Dennis Jon Beaumont, Libertyville, IL (US); John Thaddeus Filiczkowski, Spring Grove, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/044,019

(22) Filed: Feb. 15, 2016

(65) Prior Publication Data

US 2017/0232126 A1     Aug. 17, 2017

(51) Int. Cl.
*A61L 9/03*     (2006.01)
*H05B 1/00*     (2006.01)
*F21V 35/00*     (2006.01)
*C11C 5/00*     (2006.01)

(52) U.S. Cl.
CPC ....... *A61L 9/03* (2013.01); *C11C 5/00* (2013.01); *F21V 35/00* (2013.01); *H05B 1/00* (2013.01); *A61L 2209/135* (2013.01)

(58) Field of Classification Search
CPC .. A47J 36/2461; A47J 36/2483; A47J 27/004; A61L 9/03; H05B 3/04; H05B 3/20; H05B 3/00; B29C 45/2737
USPC ............................................... 219/390, 443.1
See application file for complete search history.

(56) References Cited

U.S. PATENT DOCUMENTS

| | | | |
|---|---|---|---|
| 1,990,640 A * | 2/1935 | Doherty | A47J 36/2483 219/433 |
| 2,053,314 A | 9/1936 | Balyozian | |
| 2,866,956 A * | 12/1958 | Miller | A47J 36/2483 219/218 |
| 3,454,745 A * | 7/1969 | Stone | A45D 34/00 219/415 |
| 3,869,968 A | 3/1975 | Ihlenfeld | |
| 4,853,517 A | 8/1989 | Bowen et al. | |
| 4,861,969 A * | 8/1989 | Kicherer | F24C 15/102 219/451.1 |
| 6,053,649 A | 4/2000 | Ronai | |
| 6,121,585 A * | 9/2000 | Dam | A47G 19/2288 219/385 |
| 6,627,857 B1 | 9/2003 | Tanner et al. | |
| 6,756,567 B1 | 6/2004 | Suen | |

(Continued)

FOREIGN PATENT DOCUMENTS

| | | |
|---|---|---|
| WO | 03096748 A1 | 11/2003 |
| WO | 2011163217 A1 | 12/2011 |

(Continued)

OTHER PUBLICATIONS

International Search Report and Written Opinion dated May 11, 2017, cited in related PCT application PCT/US2017/017470 (11 pages).

*Primary Examiner* — Tuongminh N Pham
(74) *Attorney, Agent, or Firm* — Quarles & Brady LLP

(57) ABSTRACT

A wax warmer includes a reservoir for receiving a wax melt, a housing defining an interior volume and configured to receive the reservoir, and a hermetically sealed heater engine positioned within the interior volume and in thermal contact with the reservoir.

20 Claims, 18 Drawing Sheets

(56) References Cited

U.S. PATENT DOCUMENTS

| | | | |
|---|---|---|---|
| 6,935,535 B2 | 8/2005 | Pandolfi et al. | |
| 7,284,741 B2 | 10/2007 | Pierce | |
| 7,377,772 B2 | 5/2008 | Thune et al. | |
| 8,567,644 B2 | 10/2013 | Martinez de San Vicente Oliveras | |
| 8,870,029 B2 | 10/2014 | Stanojlovic et al. | |
| 9,241,243 B1* | 1/2016 | Marth | H04W 4/029 |
| 2005/0016985 A1 | 1/2005 | Haas et al. | |
| 2007/0221068 A1* | 9/2007 | Boussemart | A47J 27/004 99/279 |
| 2010/0192785 A1* | 8/2010 | Krauchi | A47J 43/042 99/453 |
| 2010/0264127 A1* | 10/2010 | Ando | A47J 27/21 219/458.1 |
| 2010/0270943 A1 | 10/2010 | Cook | |
| 2012/0070132 A1 | 3/2012 | Napier | |
| 2014/0014641 A1 | 1/2014 | Propes | |
| 2015/0108241 A1 | 4/2015 | Chase et al. | |
| 2015/0283280 A1 | 10/2015 | Belongia | |
| 2015/0305089 A1 | 10/2015 | Belongia | |

FOREIGN PATENT DOCUMENTS

| | | |
|---|---|---|
| WO | 2015095328 A1 | 6/2015 |
| WO | 2015161185 A2 | 10/2015 |

\* cited by examiner

SEALED HEATER ENGINE FOR A WAX WARMER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to a sealed heater engine for a wax warmer, and more specifically, to a hermetically sealed heater engine that inhibits water from contacting live electrical components when a wax warmer is exposed to water.

2. Description of the Background of the Invention

Candles have been used for centuries to provide illumination and pleasant aromas to the surrounding environment. At its most basic level, a candle consists of a wick dipped in wax. The wick is lit and provides light while the burning or melting wax may provide a pleasant aroma. Alternatively, unscented or scented candles or wax melts can be placed in a warmer. These candles or warmers may also be used to provide more than just illumination and/or pleasant fragrances. For instance, candles and warmers may be placed outside around a patio or deck. The wax or oil may include materials with insect repellant properties along with providing a pleasant aroma and/or illumination. Generally, users can burn or warm waxes and oils to provide desired effects to the surrounding atmosphere or environment.

Traditional warmers and candles may have some drawbacks. Candles may be forgotten and left unsupervised and may represent a fire hazard. Also, a candle flame may be extinguished with a slight breeze or gust of wind. Melted wax may splatter or make a mess with traditional candles. An additional drawback associated with candles is the inability to control the intensity of the heat being provided. A candle flame is not easily adjustable and thus the amount of heat the flame provides to the infused wax or oil does not allow a user to vary the strength of the fragrance or volatile introduced into the surrounding environment.

Some attempts have been made to overcome the aforementioned drawbacks associated with warmers and candles through the use of electric wax warmers. An electric wax warmer consists of a heater in thermal contact with a reservoir for holding a wax melt or infused oil. The heater replaces the candle in a traditional warmer and melts the wax or heats the oil in the reservoir, resulting in the same benefits as previously mentioned. The lack of a flame reduces the risk associated with traditional warmers and candles. Another advantage may be that the temperature of the heater in an electric wax warmer can be adjusted. This provides the user with more control over the amount of fragrant or other materials introduced into the surrounding environment. Electric wax warmers also have more consistent performance indoors and outdoors and are less messy than traditional candles and warmers.

Traditional electric wax warmers include a housing, commonly constructed of a ceramic, plastic or synthetic material, that encloses the various electrical components necessary for heating the wax melt or infused oil. Even if warned against using an electric wax warmer around water, users sometimes position or use such devices in environments where there is a risk of the warmer being exposed to water. An example would be near a bath tub while a user takes a bath. If the warmer were to fall or be accidentally knocked into the bath, a hazardous shock may be delivered to a user in the bath.

Attempts have been made by some standards setting organizations to require certain performance standards related to moisture and water. For example, the UL 283 standard for air fresheners and deodorizers includes sections relating to humidity and liquid tightness for containers.

Interestingly, traditional electric wax warmers often are not water resistant to prevent electric shocks, leaving the users of electric wax warmers at risk. Therefore, there is a need for an electric wax warmer that overcomes the aforementioned drawbacks. In particular, there is a need for a wax warmer that is capable of preventing electrical shocks being delivered when the electric wax warmer is accidentally exposed to water. Further, there is a need for a wax warmer that includes a hermetically sealed heater engine that is capable of preventing the ingress of water when accidentally exposed to water, such that a user is inhibited from receiving a shock from the live electrical components.

The present disclosure overcomes some of the aforementioned drawbacks by providing a sealed heater engine for an electric wax warmer that prevents water from contacting live electrical components upon accidental exposure to water. The sealed heater engine disclosed herein also minimizes the material and manufacturing costs and reduces the opportunity to expose users to electrical shocks.

SUMMARY OF THE INVENTION

According to one aspect, a wax warmer includes a reservoir for receiving a wax melt, a housing defines an interior volume and is configured to receive the reservoir, and a hermetically sealed heater engine is positioned within the interior volume and in thermal contact with the reservoir.

According to a different aspect, a warmer includes a reservoir for receiving a melt, a housing defines an interior volume and is coupled to the reservoir, and a sealed heater engine is positioned within the interior volume and in thermal contact with the reservoir, wherein the sealed heater engine includes a seal that prevents the ingress of liquids into the sealed heater engine.

According to another aspect, a warmer includes a reservoir for receiving a melt and a housing includes an upper portion and a lower portion that defines an interior volume, wherein the upper portion is coupled to the reservoir and the reservoir is positioned within the interior volume. Further, a sealed heater engine is positioned within the interior volume and in thermal contact with the reservoir, wherein the sealed heater engine includes a seal to prevent liquids from reaching electronic components contained therein.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Referring to FIGS. 1-4, a first embodiment of a wax warmer 100 is depicted. The wax warmer 100 is designed to heat a wax melt 102 (see FIG. 1) and thereby release a fragrance and/or other material contained therein into the surrounding environment. The wax warmer 100 generally includes a housing 104 and a reservoir 106 (see FIGS. 7 & 8). The wax warmer 100 is generally described to include the aforementioned components, but the wax warmer 100 may be adapted to add or remove various components according to specific user requirements.

Figure 1:
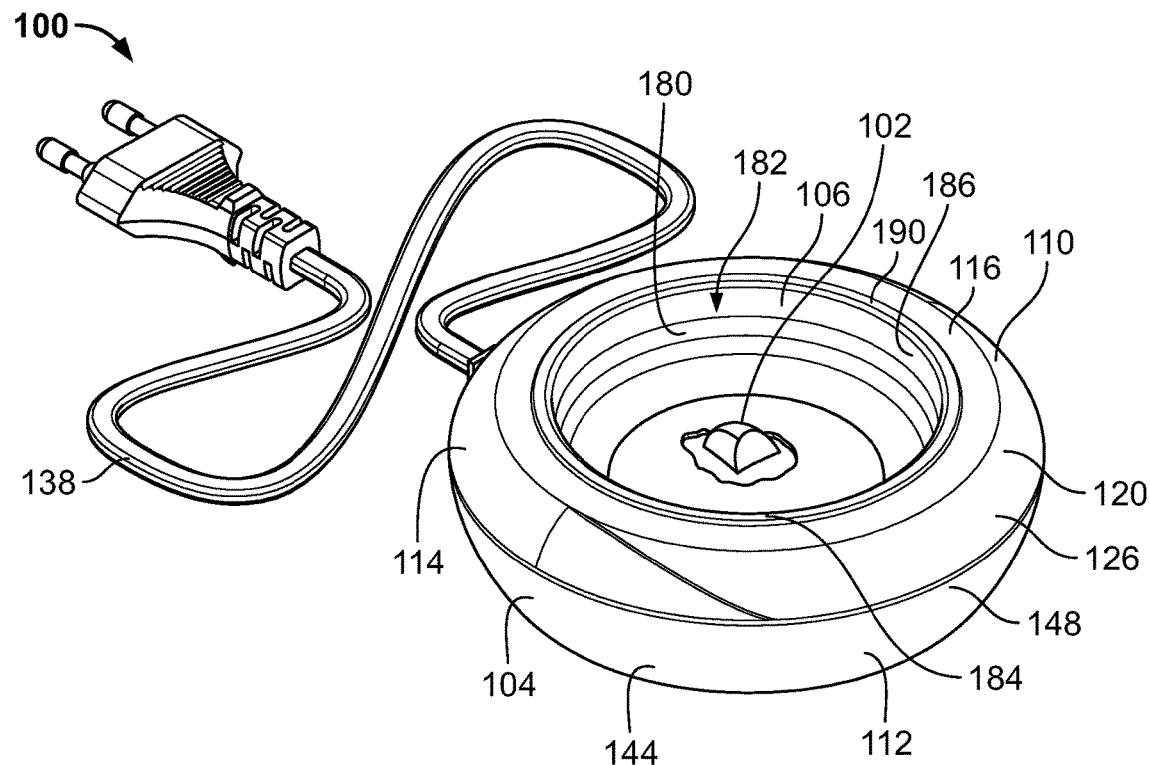
FIG. 1 is an isometric view of a top, front, and side of a first embodiment of an electric wax warmer.
Figure 2:
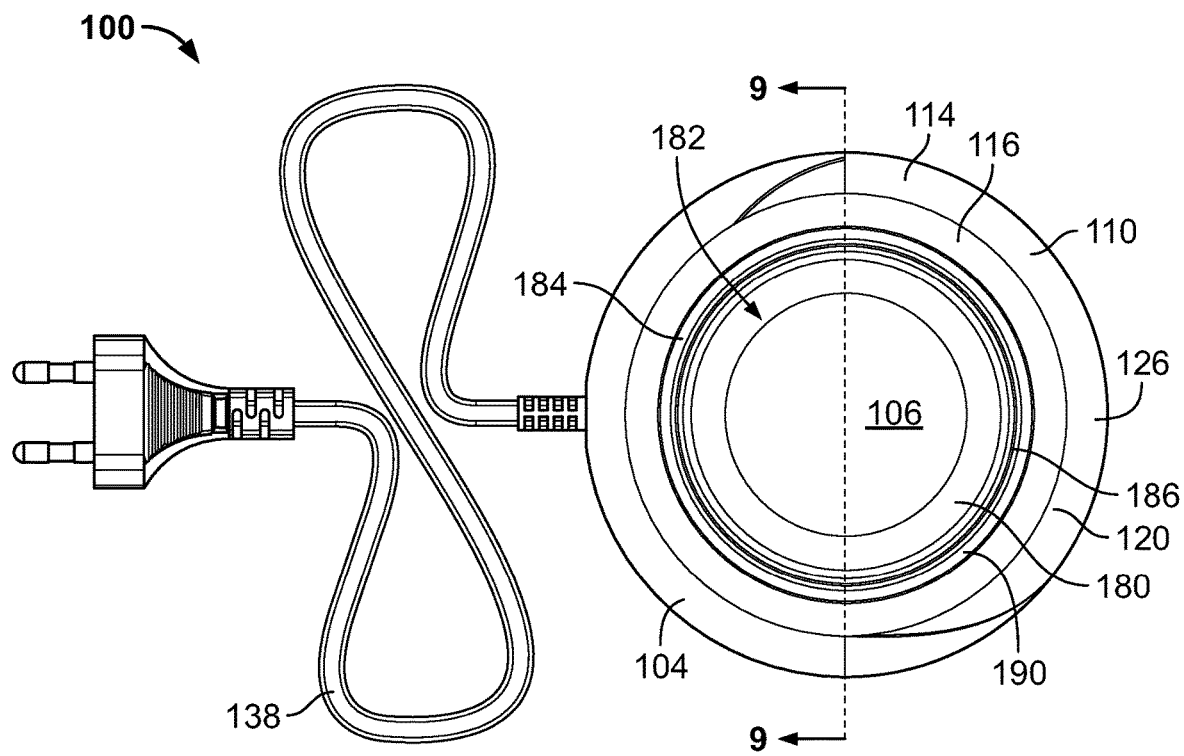
FIG. 2 is a top plan view of the electric wax warmer of FIG. 1.
Figure 3:
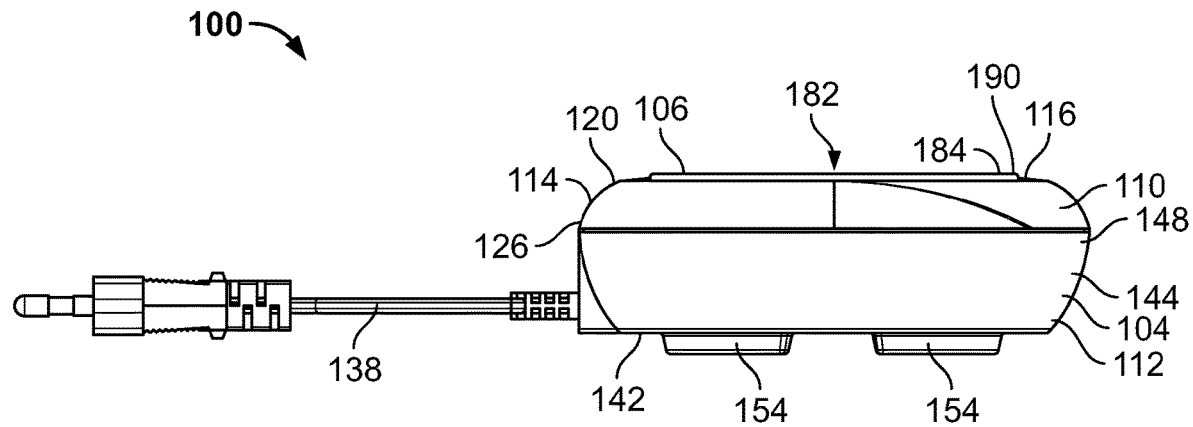
FIG. 3 is a side elevational view of the electric wax warmer of FIG. 1.
Figure 4:
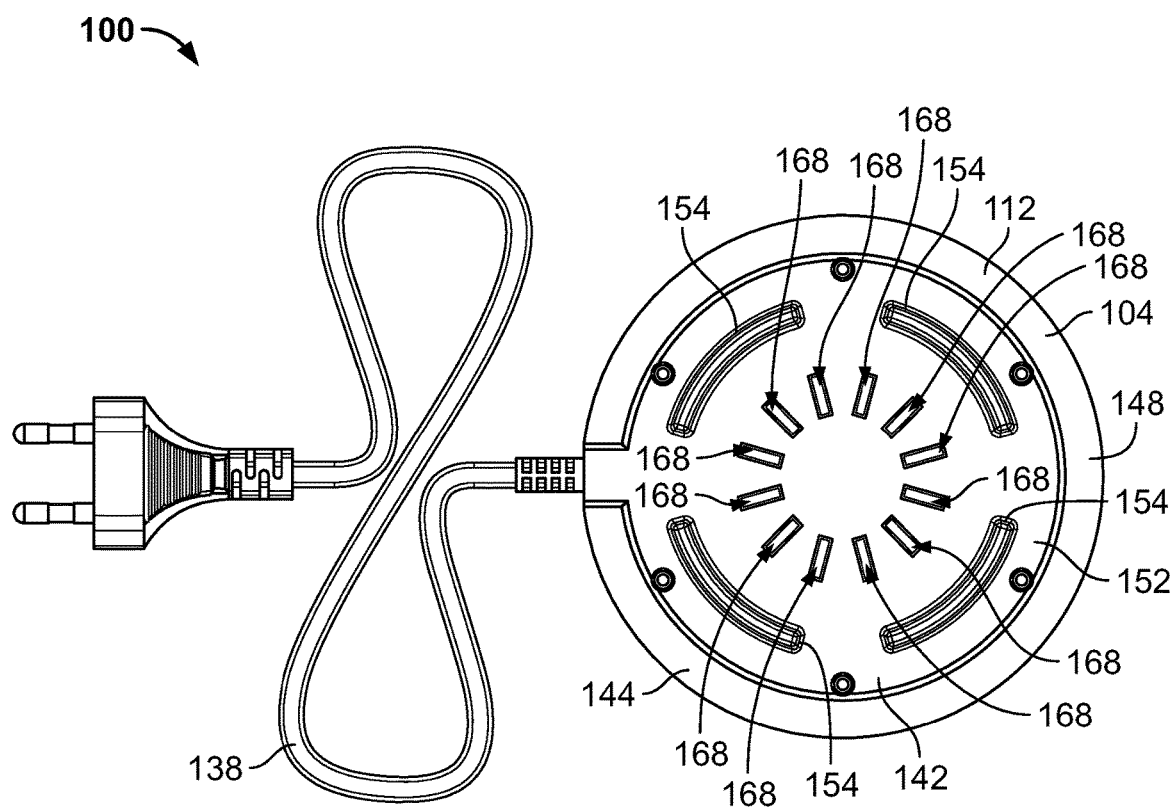
FIG. 4 is a bottom plan view of the electric wax warmer of FIG. 1.
Figure 5:
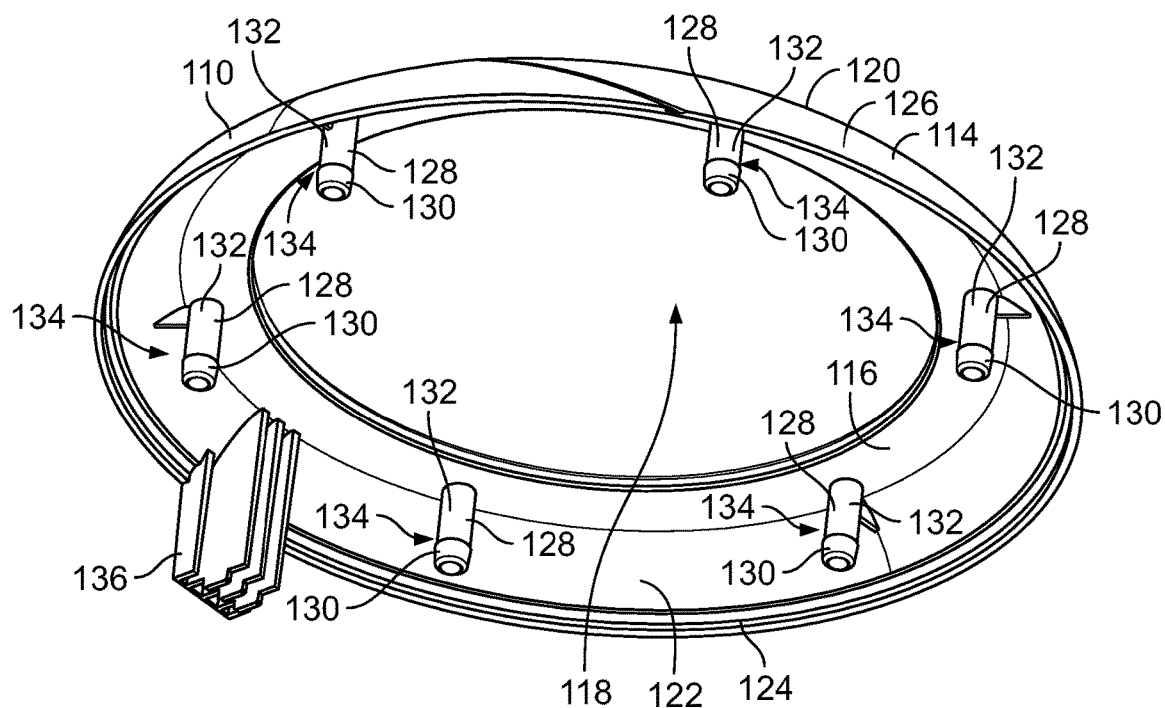
FIG. 5 is an isometric view of a bottom, front, and side of an upper housing portion of the electric wax warmer of FIG. 1.
Figure 6:
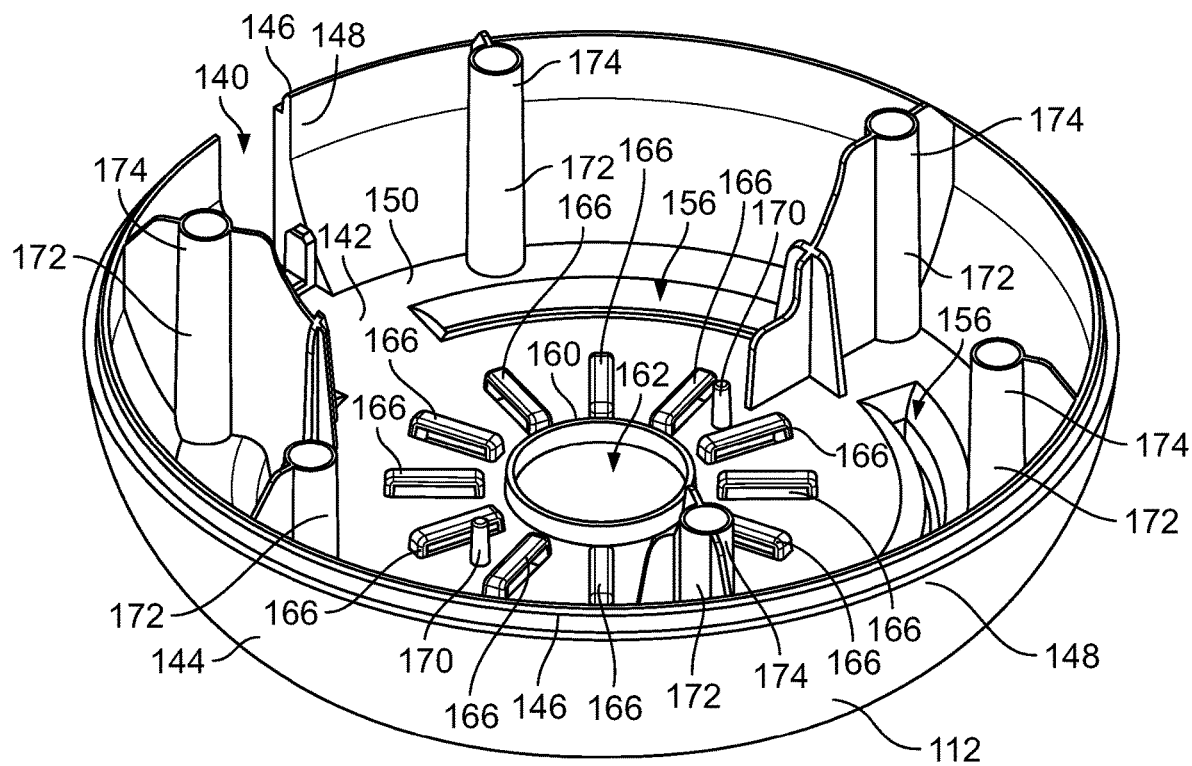
FIG. 6 is an isometric view of a top, front, and side of a lower housing portion of the electric wax warmer of FIG. 1.

Referring to FIGS. 5 and 6, the housing 104 comprises an upper housing portion 110 and a lower housing portion 112. With particular reference to FIG. 5, the upper housing portion 110 includes a first curved side wall 114 that includes an inwardly projecting flange 116, which defines an aperture 118. The aperture 118 is configured to receive the reservoir 106. The inwardly projecting flange 116 extends toward a central axis of the wax warmer 100 from an upper portion 120 of the first curved side wall 114. The first curved side wall 114 includes an inner surface 122. A cutout 124 is formed in the inner surface 122 adjacent a lower end 126 of the first curved side wall 114. The upper housing portion 110 also includes a plurality of retention cylinders 128 that extend downward from the inwardly projecting flange 116. The plurality of retention cylinders 128 includes a head portion 130 that has a slightly larger diameter than a body portion 132. A ridge 134 is formed in the body portion 132 below the head portion 130. In the present embodiment there are 6 retention cylinders depicted in FIG. 5, the use of which will be discussed below. It is contemplated that the shape and size of the wax warmer 100 will dictate the number of retention cylinders 128, i.e., smaller housings may have fewer retention cylinders, whereas larger housings may require a greater number. The upper housing portion 110 also includes a cord retention portion 136 that projects downward from the inner surface 122 of the curved side wall 114. The cord retention portion 136 cooperates with an electrical cord 138 (see FIGS. 1-4) and a cord pass through 140 of the lower housing portion 112 (see FIG. 6) to retain the electrical cord 138.

With continued reference to FIG. 6, the lower housing portion 112 includes a flat bottom 142 and a second curved side wall 144. A protrusion 146 extends from a top portion 148 of the second curved side wall 144. The protrusion 146 is configured to cooperate with the cutout 124 of the upper housing portion 110 when the upper housing portion 110 is joined with the lower housing portion 112. The flat bottom 142 includes an inner surface 150 and an outer surface 152 (see FIG. 4). A plurality of feet 154 extend from the outer surface 152 and are defined by recesses 156 in the flat bottom 142 (see FIG. 6). The recesses 156 are open to an interior volume 158 (see FIG. 9) defined by the lower housing portion 112 and the upper housing portion 110 when the wax warmer 100 is assembled. The lower housing portion 112 also includes a central annular wall 160 that defines a cup-like space 162 that is configured to retain a spacer 164 (see FIG. 9) comprised of silicone or a different heat resistant material(s).

With reference again to FIG. 6, a plurality of stops 166 is positioned around the central annular wall 160 and extend from the inner surface 150 of the flat bottom 142. The plurality of stops 166 is defined by recesses 168 formed in the flat bottom 142 and open to the exterior of the wax warmer 100 (see FIG. 4). The lower housing portion 112 also includes two cylindrical guide posts 170, the purpose of which will be discussed below. Further, the lower housing portion 112 includes a plurality of hollow retention tubes 172 that are configured to receive the plurality of retention cylinders 128 of the upper housing portion 110. An upper portion 174 of the plurality of hollow retention tubes 172 includes a narrowed portion 176 (see FIG. 9) that is configured to cooperated with the ridge 134 of the plurality of retention cylinders 128. When the upper housing portion 110 is assembled onto the lower housing portion 112, the head portion 130 of the plurality of retention cylinders 128 will cause the narrowed portion 176 to elastically deform and allow the head portion 130 to pass. As the head portion 130 passes the narrowed portion 176, the narrowed portion returns to its original state and catches the ridge 134. In this way, the upper housing portion 110 is retained securely on the lower housing portion 112.

Figure 7:
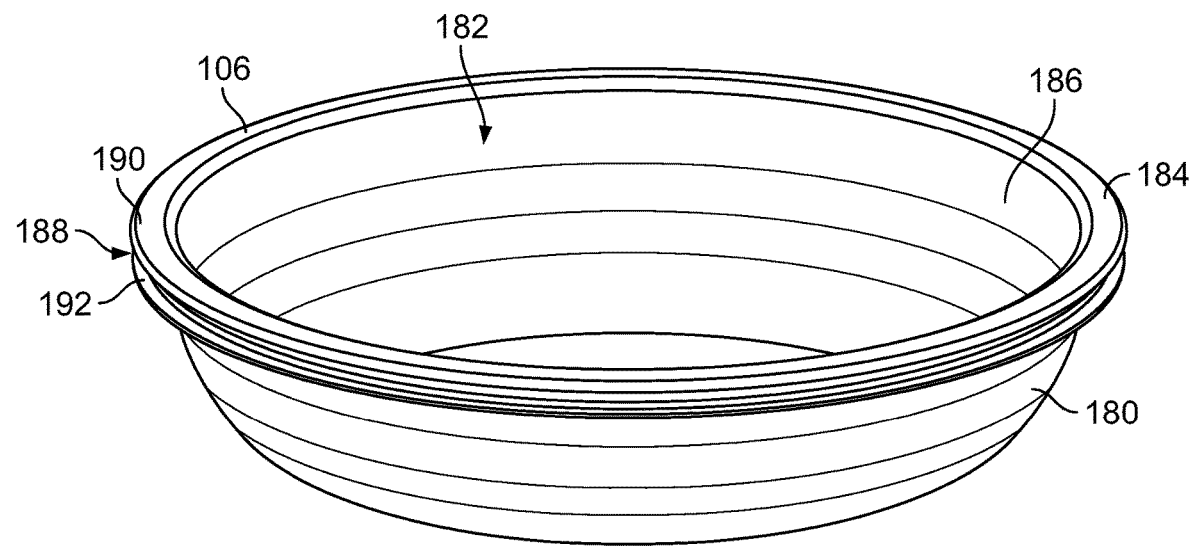
FIG. 7 is an isometric view of a top and front of a reservoir for the electric wax warmer of FIG. 1.
Figure 8:
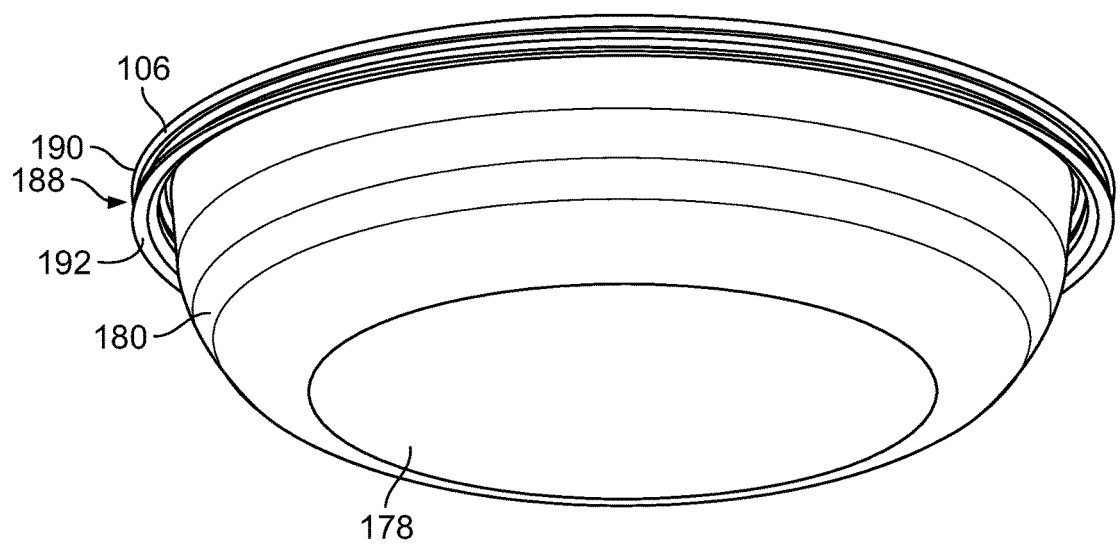
FIG. 8 is an isometric view of a bottom and front of a reservoir for the electric wax warmer of FIG. 1.

Now turning to FIGS. 7 and 8, the reservoir 106 is depicted. The reservoir 106 includes a flat bottom 178 and a third curved side wall 180 that define a reservoir volume 182 for receiving a wax melt or other scented and/or volatile materials, such as scented oils or essential oils. A reservoir flange 184 extends from a top end 186 of the third curved side wall 180. The reservoir flange 184 is configured to form a c-shaped channel 188 that extends around the entire perimeter of the reservoir 106. The c-shaped channel 188 is configured to receive the inwardly projecting flange 116 of the upper housing portion 110 (see FIG. 9). When the reservoir 106 is assembled with the upper housing portion 110, a top lip 190 of the c-shaped channel is above the inwardly projecting flange 116 and a bottom lip 192 is below the inwardly projecting flange 116, thereby securely coupling the reservoir 106 to the upper housing portion 110.

Figure 9:
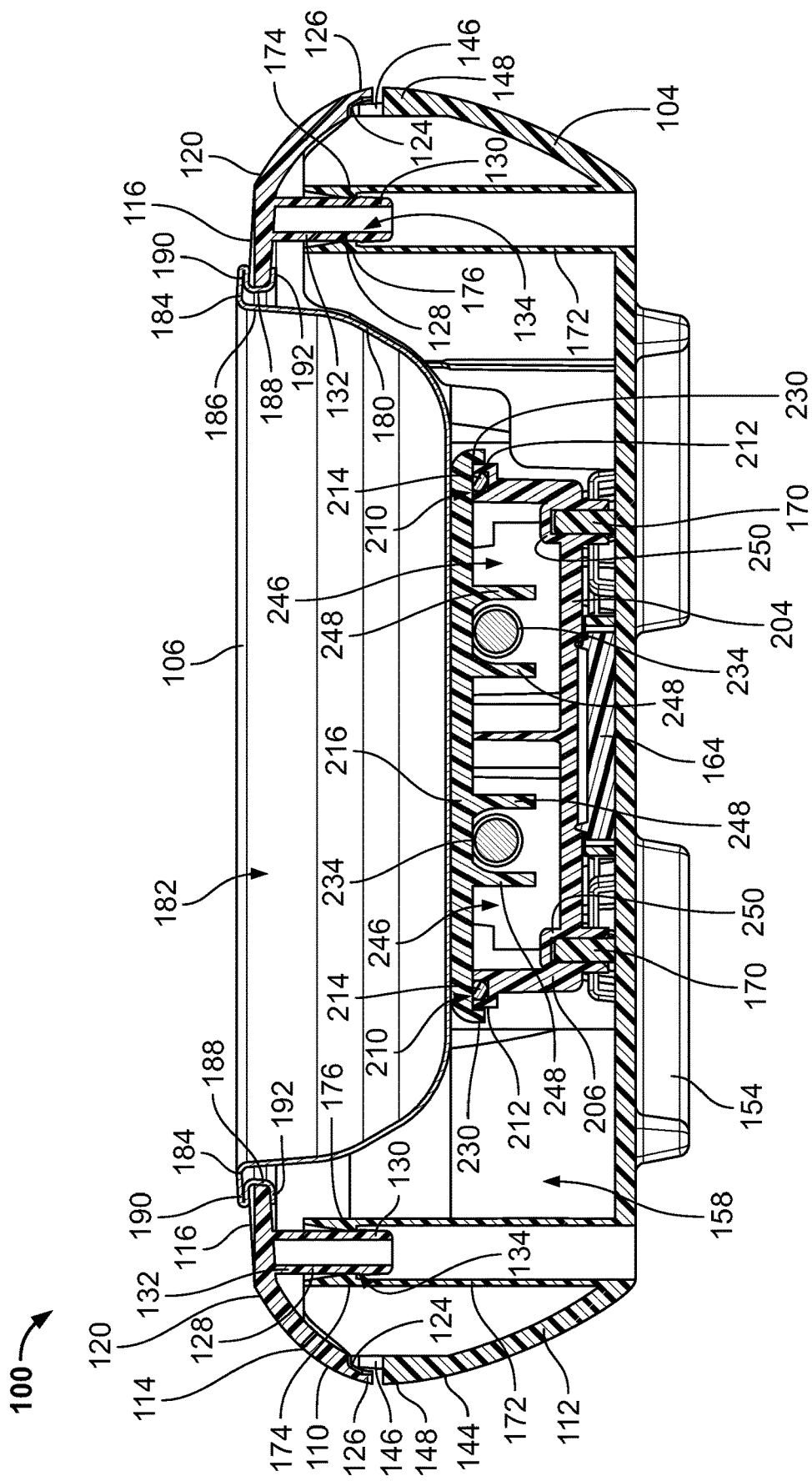
FIG. 9 is a cross-sectional view of the electric wax warmer of FIG. 1 taken along the line 9-9 of FIG. 2.
Figure 10:
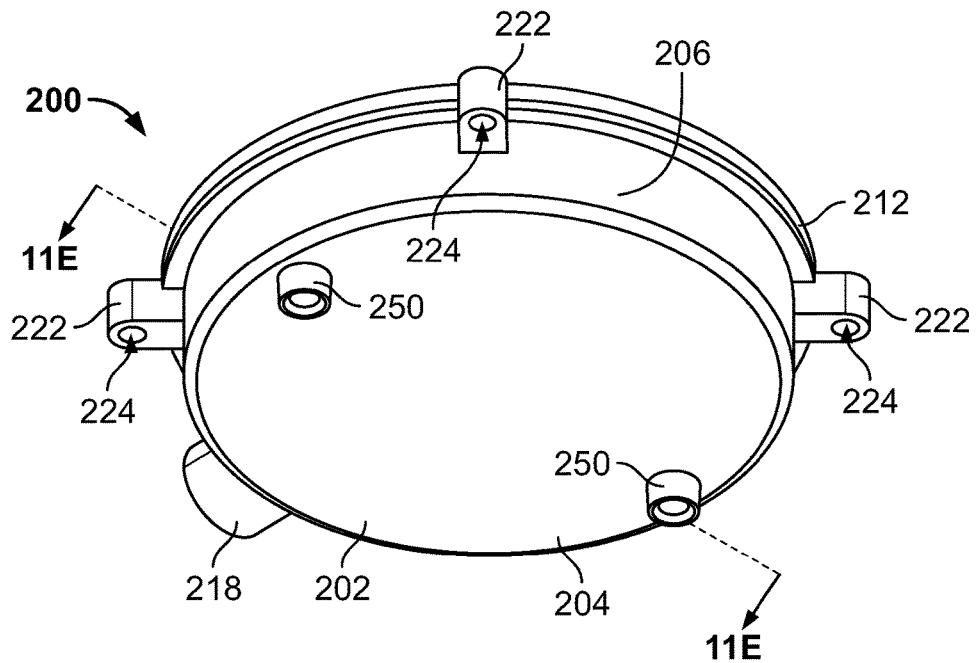
FIG. 10 is an isometric view of a bottom and front of a first embodiment of a sealed heater engine for the electric wax warmer of FIG. 1.
Figure 11A:
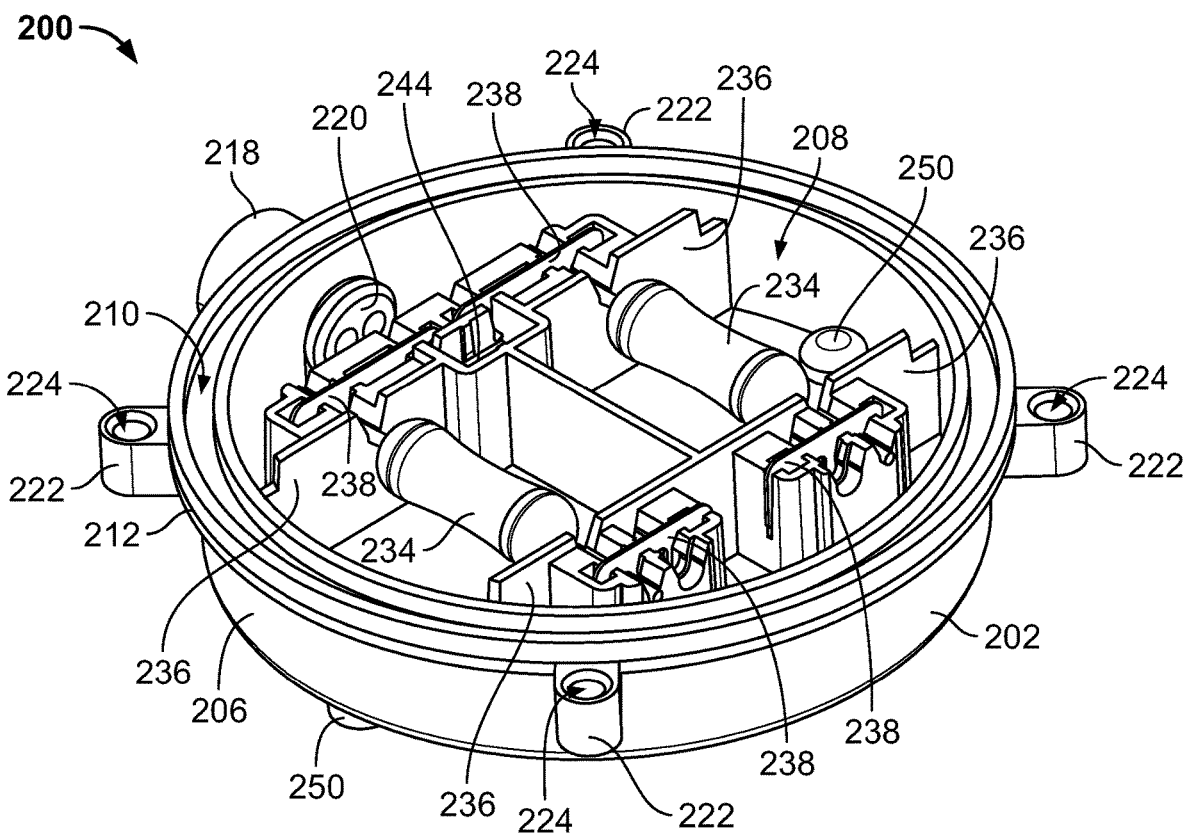
FIG. 11A is an isometric view of a top and front of a sealed heater engine for the electric wax warmer of FIG. 1 having a top cover removed to expose electrical components contained within.
Figure 11B:
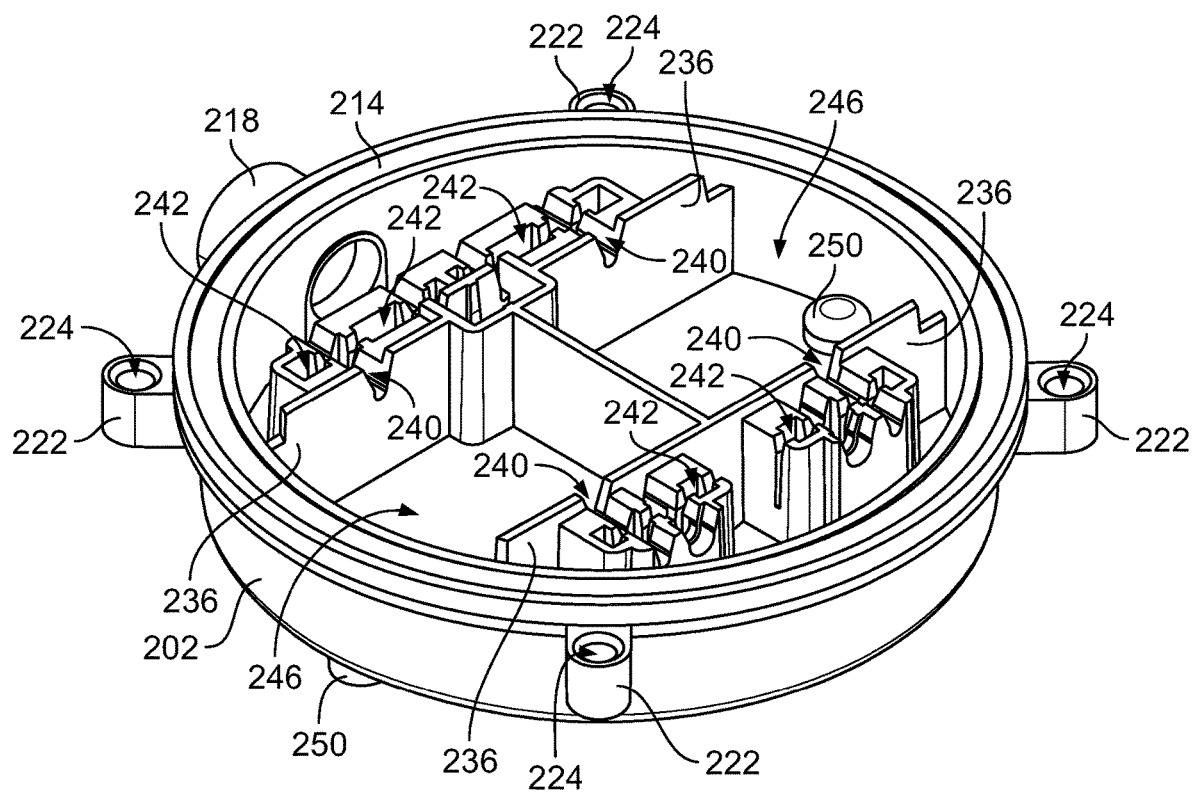
FIG. 11B is an isometric view of a top and front of a base portion of the sealed heater engine of FIG. 11A.
Figure 11C:
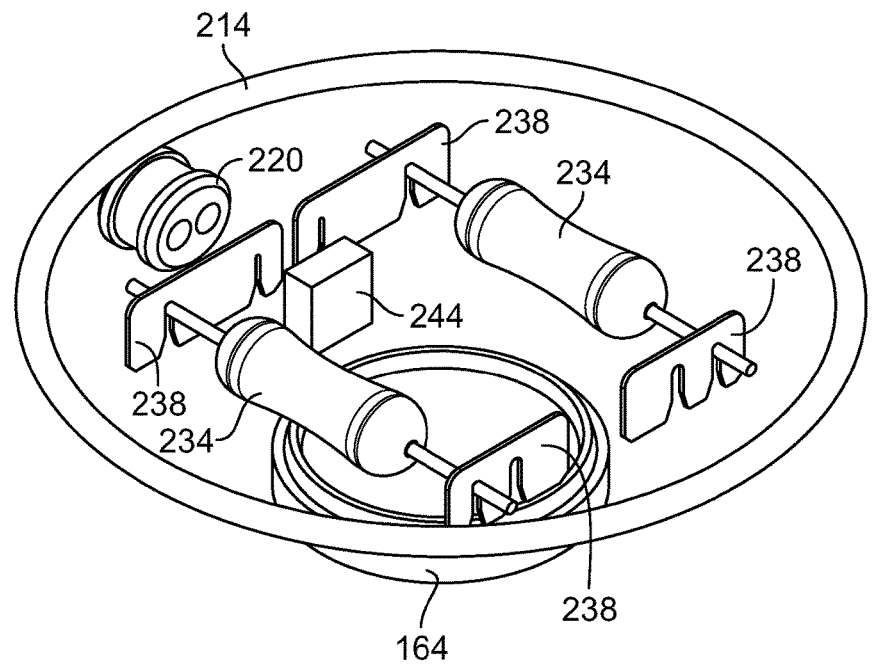
FIG. 11C is an isometric view of a top, front, and side of the electrical components and seals of the sealed heater engine of FIG. 11A.
Figure 11D:
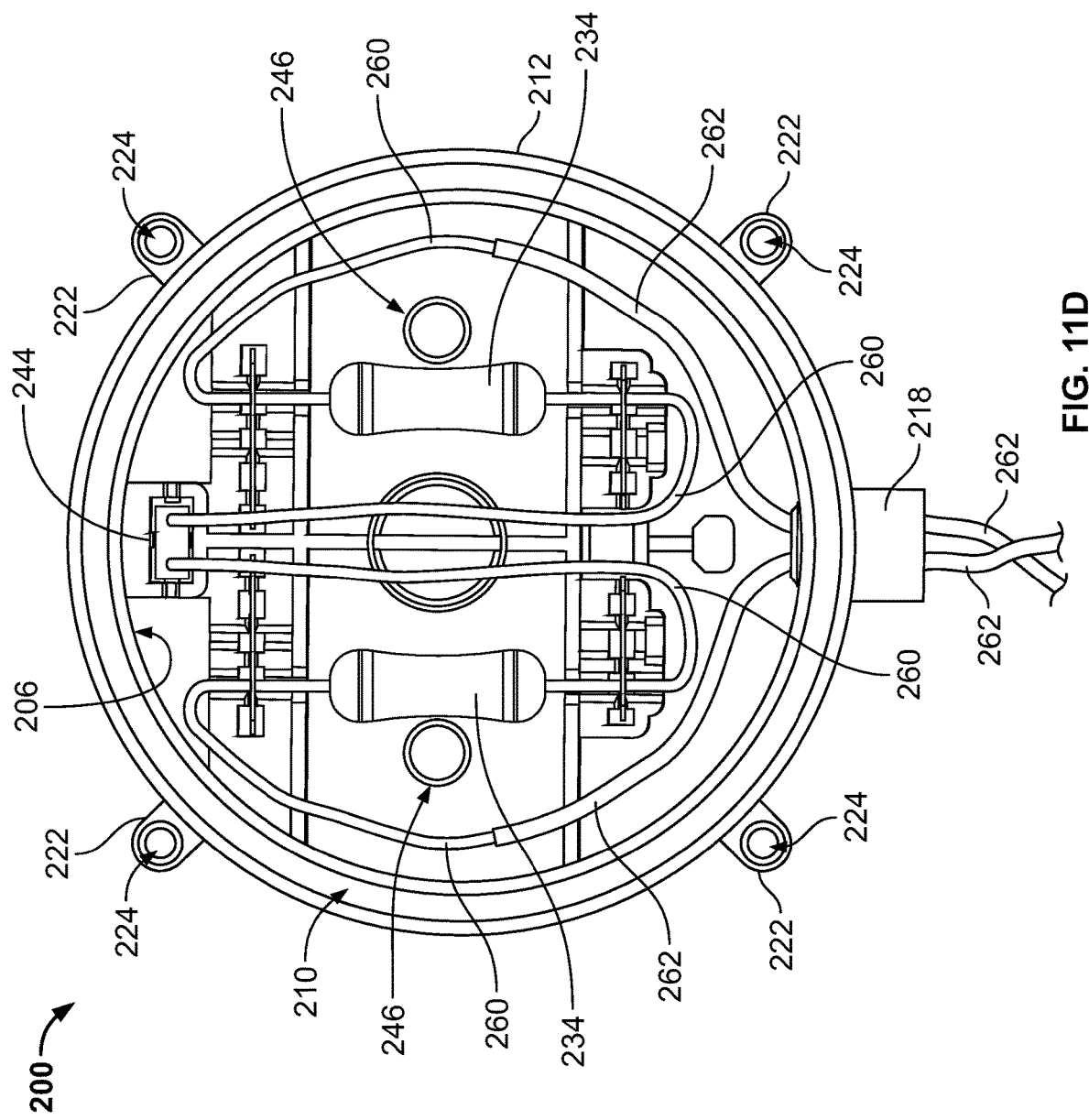
FIG. 11D is a top plan view of the sealed heater engine of FIG. 11C with an alternative electrical component configuration.
Figure 11E:
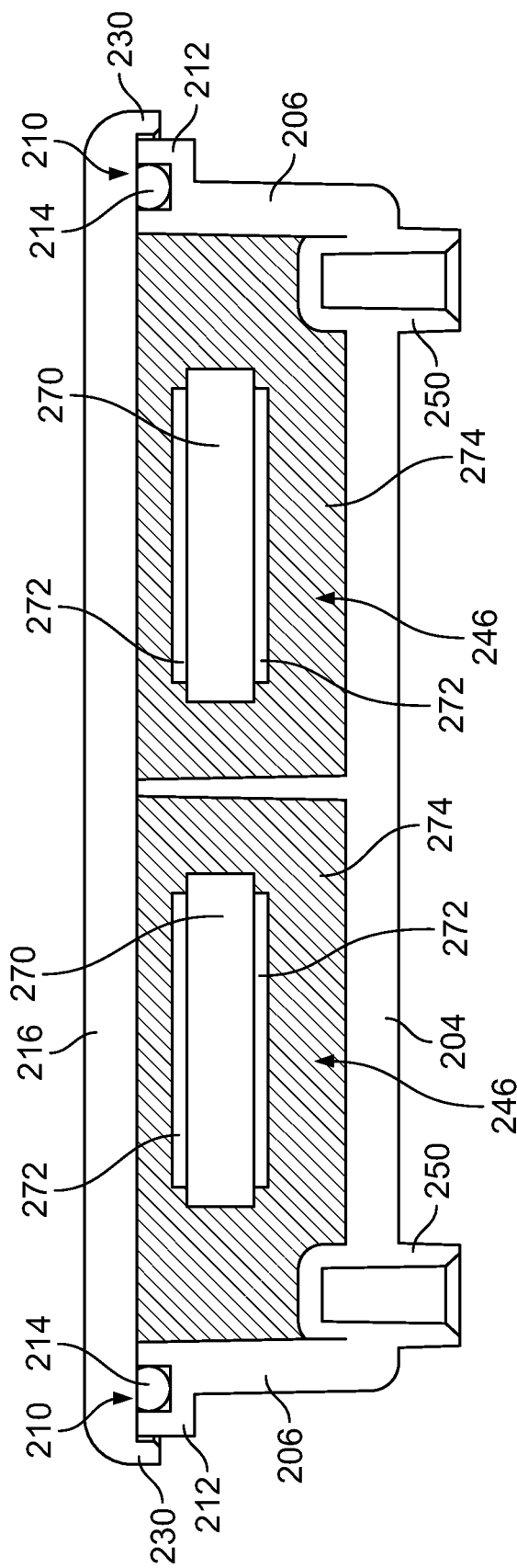
FIG. 11E is a cross-sectional view of the sealed heater engine of FIG. 10 taken along the line 11E-11E of FIG. 10 depicting another embodiment of the electrical components.
Figure 12:
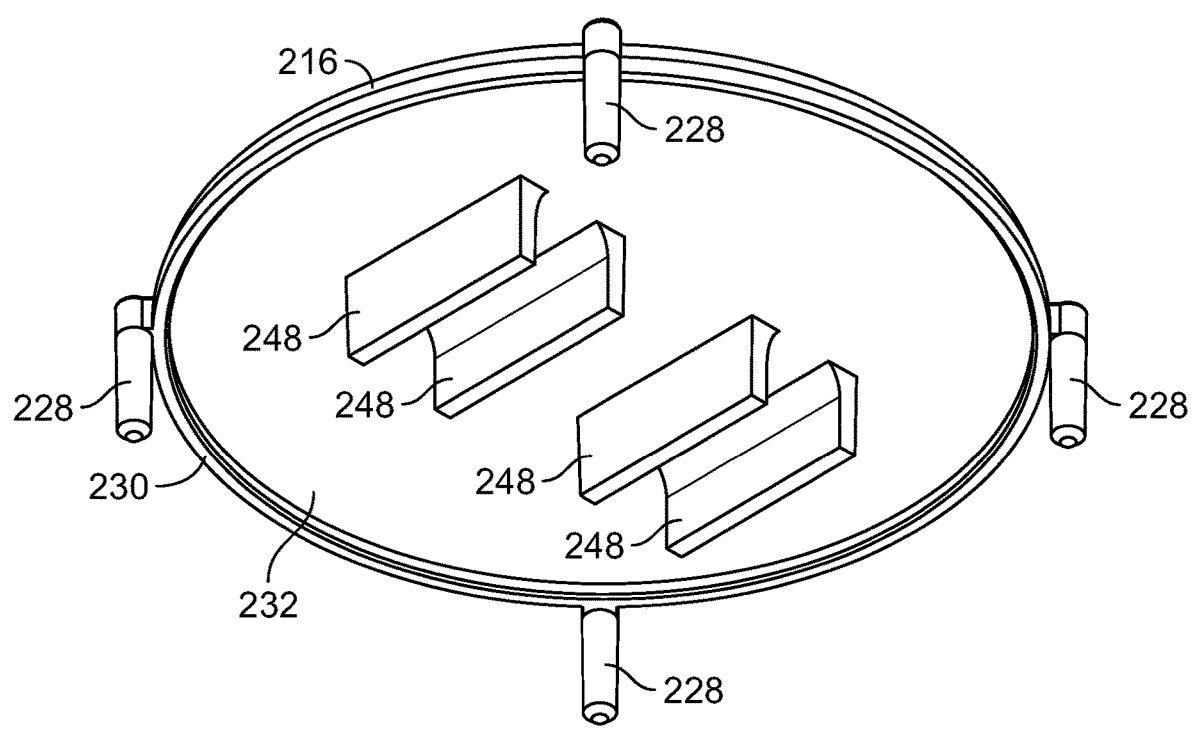
FIG. 12 is an isometric view of a bottom and front of the top cover of the sealed heater engine for the electric wax warmer of FIG. 1.

Turning now to FIGS. 10-12, a sealed heater engine 200 is depicted. The sealed heater engine 200 includes a base portion 202 having a flat bottom 204 and a side wall 206 that define a heater engine interior volume 208 (see FIG. 11A). A channel 210 is defined in a top end 212 of the side wall 206. The channel 210 is configured to receive an o-ring seal 214 (see FIG. 9) that forms a first seal between the base portion 202 and a top cover 216 (see FIG. 12). With reference again to FIG. 11A, a pass through 218 is formed in the side wall 206 to allow electrical lines (not shown) from the electrical cord 138 to extend into the sealed heater engine 200. The pass through 218 includes a wire seal 220, the end of which is visible in FIG. 11A. The wire seal 220 prevents any moisture or liquids from entering into the interior volume 208 of the heater engine 200. The base portion 202 also includes a plurality of guides 222 that extend outwardly from the side wall 206. Each of the plurality of guides 222 defines a cylindrical hole 224. The top cover 216 includes a plurality of alignment cylinders 228 that are positioned around the top cover 216 perimeter. The top cover 216 also may include a ridge 230. The top cover 216 and the ridge 230 are sized such that the alignment cylinders 228 can be positioned within the cylindrical holes 224 and the ridge 230 fits around the top end 212 of the side wall 206 when the top cover is assembled onto the base portion 202 (see FIG. 9). The ridge 230 is in contact with the top end 212 of the side wall 206 and an underside 232 of the top cover 216 is in contact with the o-ring seal 214 when the sealed heater engine 200 is assembled.

Referring to FIGS. 11A-C, in some embodiments the sealed heater engine 200 may include one or more resistors 234 that are held in place by walls 236 and clips 238. The walls 246 include a v-notch 240 (see FIG. 11B) and the clips 238 (see FIG. 11C) are configured to fit over wire ends of the resistors 234 and into retention spaces 242 (see FIG. 11B). The sealed heater engine 200 may also include a thermal cut off (TCO) and/or fuse 244 as means of regulating the temperature and preventing the sealed heater engine 200 from overheating (see FIG. 11A). The clips 238 may also act as connectors for the wires (not shown) that complete the circuit between the electrical cord 138, resistors 234, and the TCO and/or fuse 244. One having ordinary skill in the art would understand the many different ways the required circuit may be connected. The walls 236 in cooperation with the side wall 206 delineate heating chambers 246 (see FIG. 11B) that define the space around the resistors 234. It is contemplated that in some embodiments, the heating chambers 246 may be filled with electrical potting materials (not shown) that further encase the resistors 234. One having ordinary skill in the art would understand the wide variety of potting materials that have the correct thermal and chemical properties for the present application. It is also contemplated that the clips 238 may be replaced by wire splices or any other type of electrical connector to complete any necessary circuits. Referring to FIG. 12, in some embodiments the top cover 216 may include a plurality of retention walls 248 that extend from the underside 232 of the top cover 216. The plurality of retention walls 248 may be positioned to fit around the one or more resistors 234. It is contemplated that the plurality of retention walls 248 may cooperate with the walls 236 to act as the primary means of retaining the one of more resistors 234 in the proper location.

It is also contemplated that in some embodiments the sealed heater engine 200 may include a wide variety of elements and/or devices to generate heat from a supplied electrical current. For example, in some embodiments, a heating circuit may include a resistive heating element or a PTC heater. It is further contemplated that other heating options known to those of ordinary skill in the art may be used.

The sealed heater engine 200 includes at least two alignment cylinders 250 (see FIG. 10) that extend from the flat bottom 204 of the base portion 202. The alignment cylinders 250 are sized and positioned to receive the at least two cylindrical guide posts 170 of the lower housing portion 112. The alignment cylinders 250 extend through the flat bottom 204 and into the heating chambers 246. The portions of the alignment cylinder 250 that extend into the heating chambers 246 are capped to allow the cylindrical guide posts 170 to fully seat without exposing the heating chambers 246 to the outside.

The wax warmer 100 is assembled in the following process. First, the resistors 234 and TCO and/or fuse 244 are inserted into the proper locations within the base portion 202 and connected to form a circuit either using clips 238 or other methods such as splices or soldering (not shown). In embodiments with potting materials, the potting materials are prepared and poured into the heating chambers 246 until the resistors 234 are completely encapsulated. Next, the ends of the electrical cord 138 are fed through the wire seal 220, which is inserted in the pass through 218. Subsequently, the ends of the electrical cord 138 are connected to the circuit and the wires are dressed (not shown). The o-ring seal 214 is then placed into the channel 210 and the top cover 216 is attached to the base portion 202 by inserting the alignment cylinders 228 into the cylindrical holes 224. The sealed heater engine 200 is then compressed to ensure that the top cover 216 is in contact with the o-ring seal 214 and the top of portions defining the channel 210. The is then ultrasonically welded or otherwise permanently joined to the base portion 202.

Next, the reservoir 106 is inserted into the aperture 118 of the upper housing portion 110 from below so that the bottom lip 192 catches on the inwardly projecting flange 116 of the upper housing portion 110 (see FIG. 9). The top lip 190 is then formed into its final configuration to capture the inwardly projecting flange 116 in the c-shaped channel 188 by performing several successive rolling/forming operations. Thereafter, the spacer 164 is inserted into the cup-like space 162 and the sealed heater engine 200 is placed into the lower housing portion 112 with the two cylindrical guide posts 170 positioned within the alignment cylinders 250. Then, the upper housing portion 110 is placed over the lower housing portion 112 so as to align the plurality of retention cylinders 128 of the upper housing portion 110 with the plurality of retention tubes 172. The upper housing portion 110 is then pressed onto the lower housing portion 112 until the retention cylinders 128 are fully seated within the retention tubes 172 as described above. Finally, the lower housing portion 112 and the upper housing portion 110 are joined through ultrasonic welding at the narrowed portions 176 of the retention tubes 172 and the interface of the cutout 124 of the upper housing portion 110 and the protrusion 146 of the lower housing portion 112.

Referring now to FIG. 11D, another embodiment of the electrical components is depicted for the sealed heater engine 200. The one or more resistors 234 are positioned within the heating chambers 246 as previously described. However, in the present embodiment, the TCO or fuse 244 is located in a different position proximate to the side wall 206. Also, the clips 238 have been replaced by wire crimp-type connectors 260. Further, a circuit is formed by the wires 262 connecting the depicted electrical components and the electrical cord 136. It is further contemplated that the heating chambers 246 of this embodiment may also be filled with potting material to encapsulate the one or more resistors 234.

Turning now to FIG. 11E, a cross-sectional view of another embodiment of electrical components for the sealed heater engine 200 is depicted. In this embodiment, the one of more resistors 234 have been replaced with one or more PTC heating elements 270. Electrodes 272 are shown coupled to the PTC heating elements 270. FIG. 11E also depicts the heating chambers 246 filled with potting material 274 that encapsulates the PTC heating elements 270. It is contemplated that any shape and size of PTC heating elements 270 that provide the required thermal properties and capabilities may be utilized. Further, as depicted earlier, the top cover 216 may include a plurality of retention walls 248 (not shown) that are configured for the specific geometry of the PTC heating elements.

It is contemplated that the disclosed construction and assembly of the sealed heater engine 200 and the wax warmer 100 will allow for meeting or exceeding the standards relating to water resistance in UL 283 entitled "Standard for Air Fresheners and Deodorizers" and IEC 60335 entitled "Household and similar electrical appliances—Safety." Specifically, the sealed heater engine 200 and the wax warmer 100 will meet or exceed the requirements for passing section 37 of UL 283. Also, the sealed heater engine 200 and the wax warmer 100 will meet or exceed the requirements for passing EN60335. The combination of the o-ring seal 214, the wire seal 220, and ultrasonically welding the top cover 216 to the base portion 202 results in the sealed heater engine 200 being hermetically sealed. That is, the seal created will prevent, or substantially prevent, the ingress of water or other liquids into the sealed heater engine 200 that the sealed heater engine 200 may be accidentally exposed to. Further, it is also contemplated that the ultrasonic welding of the upper housing portion 110 and the lower housing portion 112 in combination with the formation of the c-shaped channel 188 of the reservoir 106 around the inwardly projecting flange 116 will also provide a degree of water resistance to the wax warmer 100.

It is also contemplated that the wax warmer 100 could be fashioned in numerous different manners, including in different shapes than those depicted in FIGS. 1-4. For example, the wax warmer 100 may be triangular, rectangular, polygonal, star-shaped, crescent-shaped, irregularly-shaped, flower-shaped, etc. Further, a wide variety of materials may be used for the different components. The o-ring seal 214 and the wire seal 220 may be formed out of silicone or any other appropriate materials that have the necessary physical and thermal properties. Further, the housing 104 and the sealed heater engine 200 may be constructed of a wide variety of plastics including PET. Further, the reservoir 106 may be constructed out a variety of plastics or metals in different embodiments. One having ordinary skill in the art would understand the varying materials that could be employed for different components of the wax warmer 100.

Figure 13:
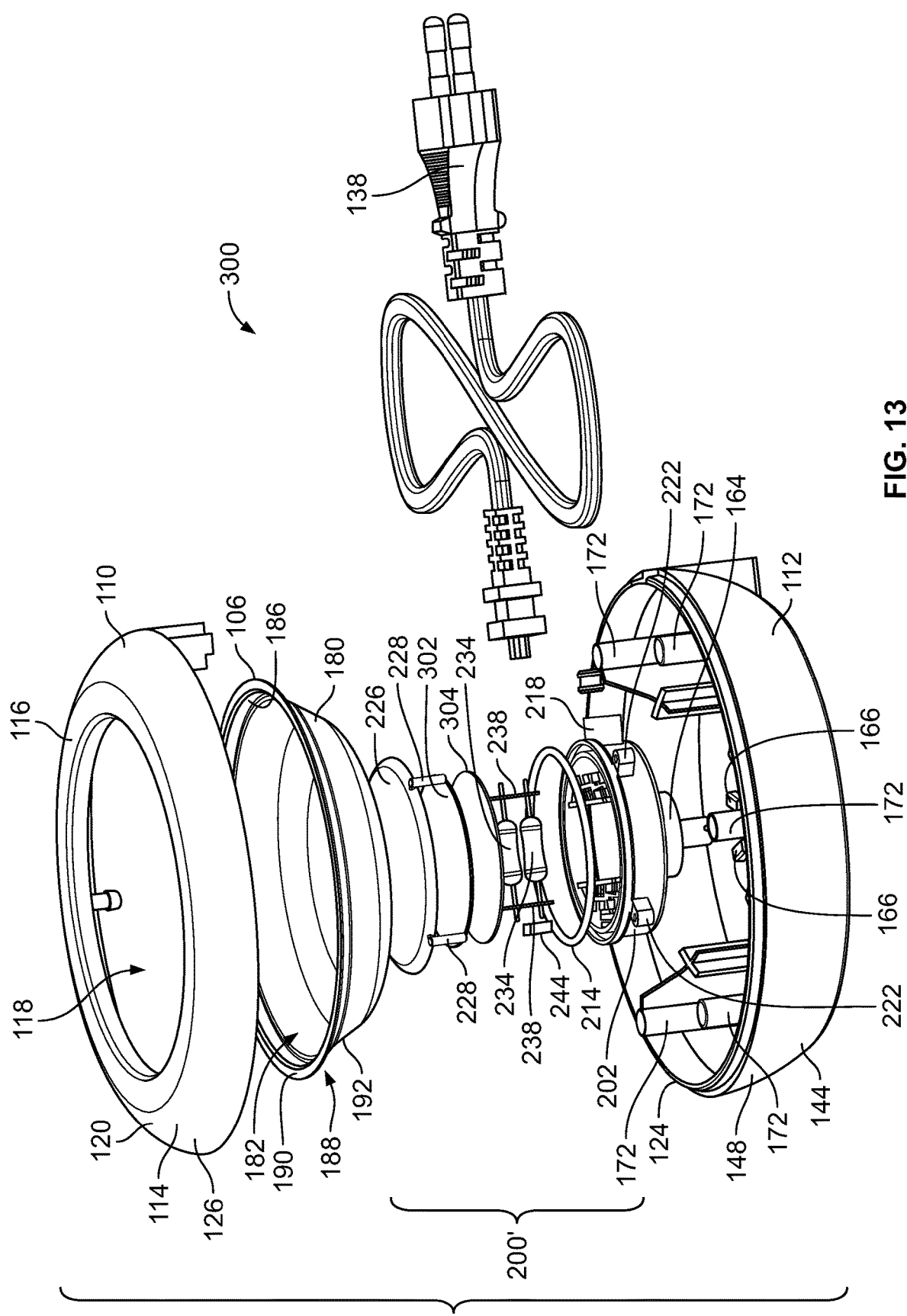
FIG. 13 is an exploded, isometric view of a wax warmer similar to the wax warmer of FIG. 1 having a second embodiment of a sealed heater engine.

Turning now to FIG. 13, an embodiment of a wax warmer 300 similar to the wax warmer 100 is depicted. The wax warmer 300 includes an upper housing portion 110, a reservoir 106, a lower housing portion 112, a silicone spacer 164, and an electrical cord 138 that function as previously discussed. Further, the wax warmer 300 includes a second embodiment of a sealed heater engine 200', which includes a top cover 216, resistors 234, a TCO and/or fuse 244, an o-ring seal 214, a wire seal 220, and a base portion 202 having a pass through 218. The sealed heater engine 200' is assembled and constructed in a similar manner, and with similar materials, as discussed above in connection with the engine 200. However, in the present embodiment, the sealed heater engine 200' of the wax warmer 300 includes a metal heat plate 302 and a Kapton™ or Mica insulating layer 304 to assist in evenly spreading the heat produced and transferring the heat from the sealed heater engine 200' to the reservoir.

Figure 14:
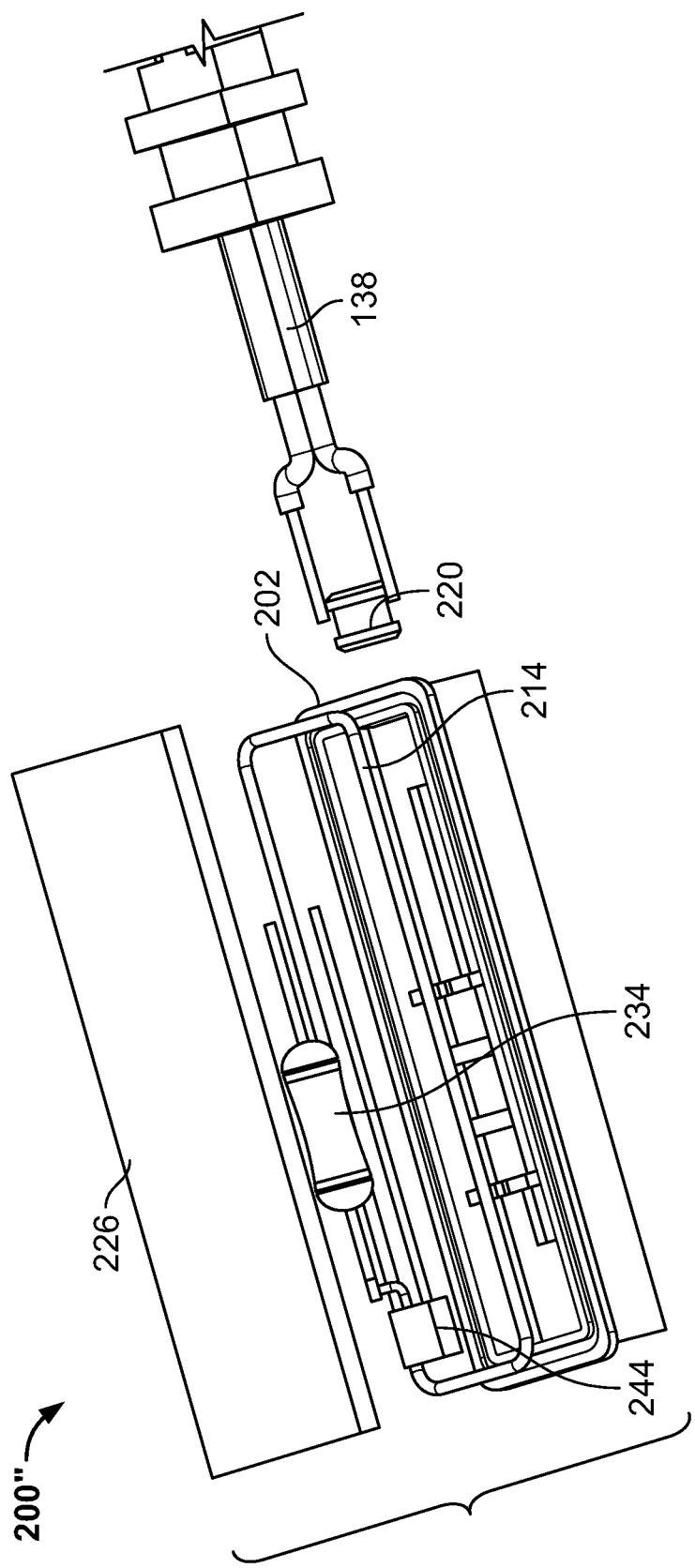
FIG. 14 is an exploded, elevational view of a third embodiment of a sealed heater engine.

Turning now to FIG. 14, a third embodiment of a sealed heater engine 200" is depicted. The sealed heater engine 200" includes a top cover 216, a base portion 202, an o-ring seal 214, a wire seal 220, a TCO and/or fuse 244, and a single resistor 234 for a heating element. Power is provided with an electrical cord 138. The sealed heater engine 200" depicted in FIG. 14 may also be constructed in a similar manner as the earlier described embodiments, including utilizing ultrasonic welding to join the top cover 216 to the base portion 202. One advantage of the present embodiment is that it may be used in wax warmers that are smaller in size. It is further contemplated that the sealed heater engine 200" of the present embodiment may also include a metal heat plate and or an insulating layer (not shown) as described in the embodiment of FIG. 13.

Figure 15:
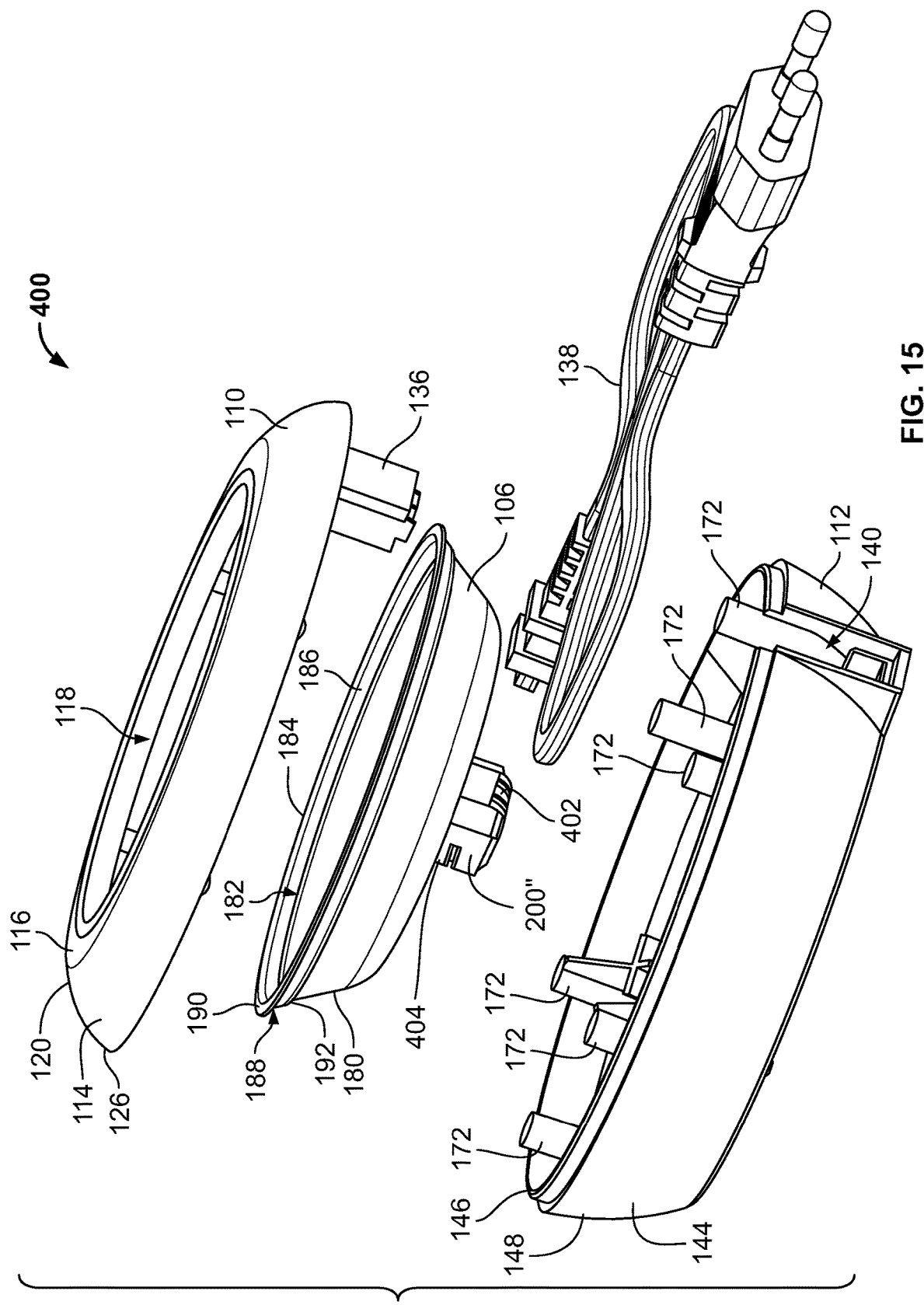
FIG. 15 is an exploded, isometric view of a second embodiment of an electric wax warmer having the sealed heater engine of FIG. 14.
Figure 16:
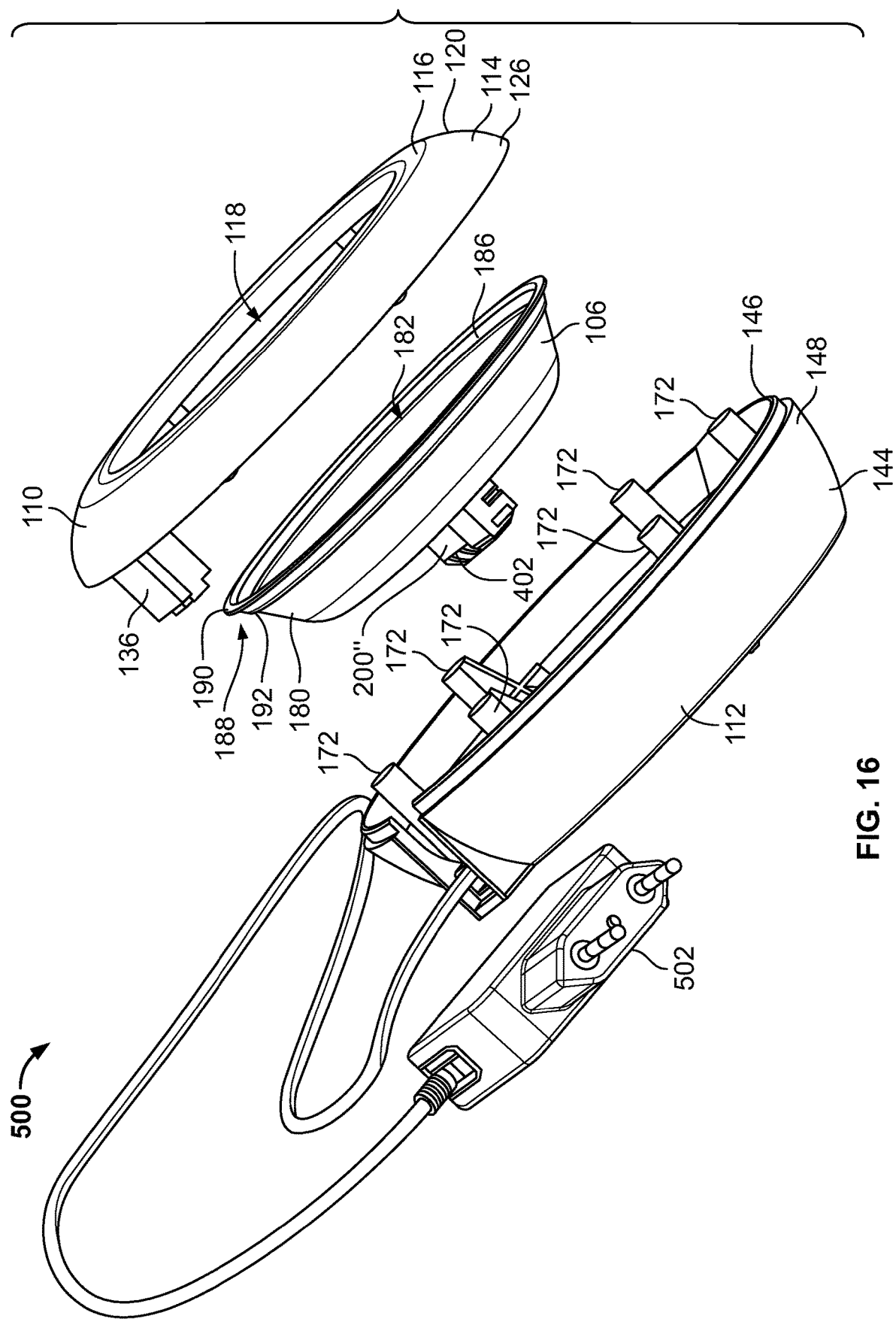
FIG. 16 is an exploded, isometric view of the electric wax warmer of FIG. 15 having the sealed heater engine of FIG. 14 and configured with a DC power supply.

Turning now to FIGS. 15 and 16, wax warmers 400 and 500, respectively, are depicted. The wax warmers 400 and 500 are similar in structure to the wax warmer 100, but include the smaller sealed heater engine 200" of FIG. 14. Specifically, the wax warmer 400 includes an upper housing portion 110, a lower housing portion 112, a reservoir 106, and an electrical cord 138. The sealed heater engine 200" is retained in thermal contact with the reservoir 106 by a metal strap 402. Thus, the assembly and construction of the wax warmer 400 is simplified as compared to other embodiments. In some embodiments a mica or insulating layer 404 may be positioned between the sealed heater engine 200" and the reservoir 106. The wax warmer 500 depicted in FIG. 16 is identical to the wax warmer 400, except that a DC transformer 502 is additionally provided. The DC transformer 502 provides a low voltage output that acts as an additional safety feature.

Figure 17:
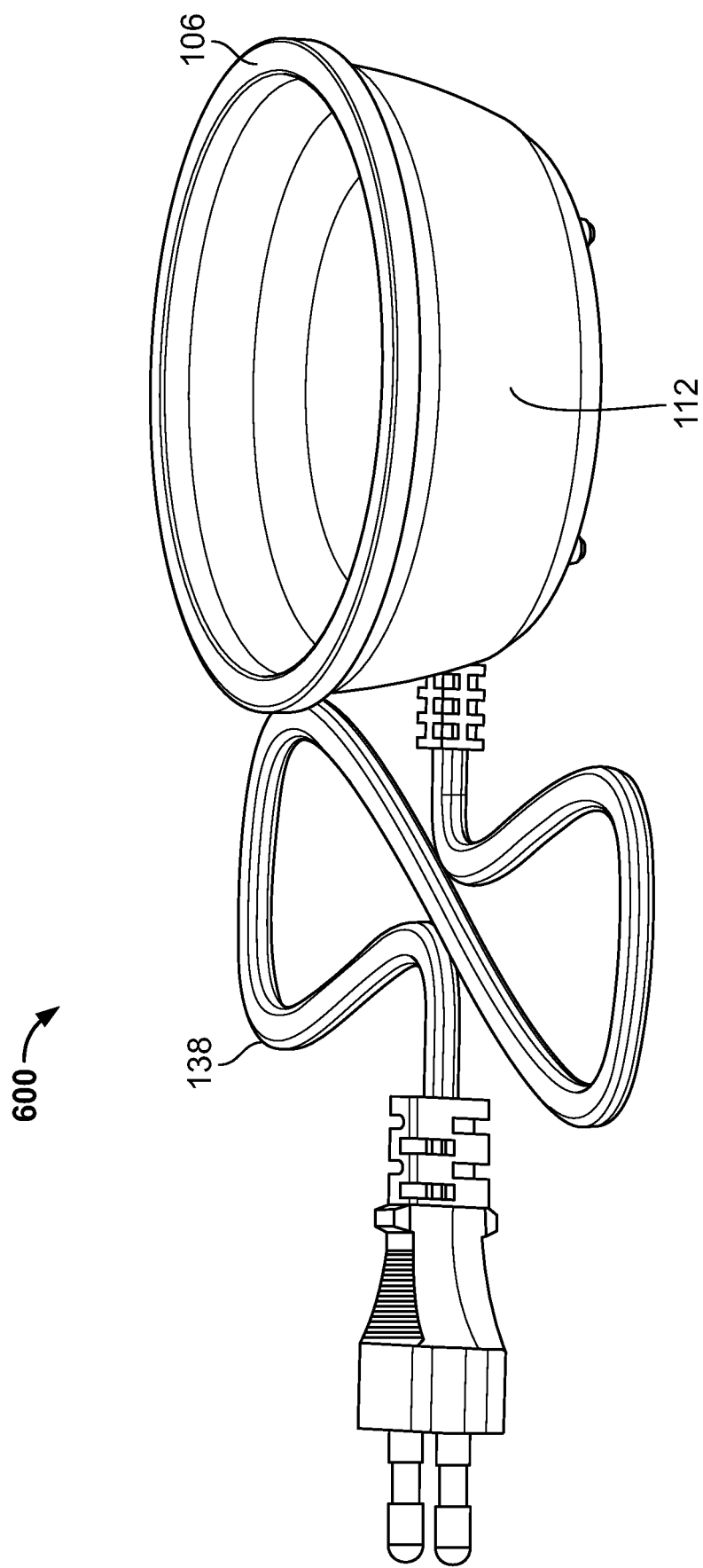
FIG. 17 is an isometric view of a top and side of a third embodiment of an electric wax warmer.
Figure 18:
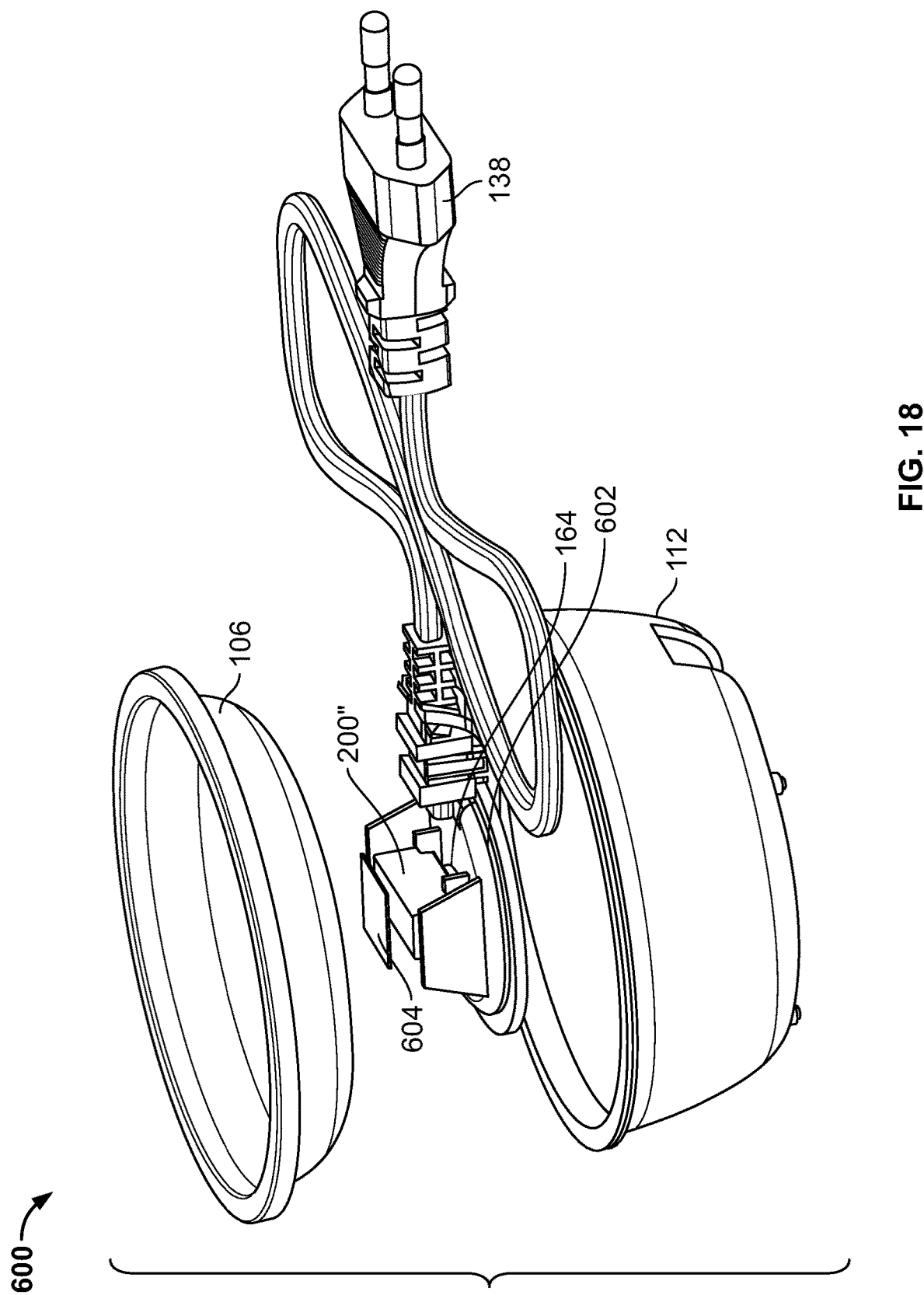
FIG. 18 is an exploded, isometric view of the electric wax warmer of FIG. 17 having the sealed heater engine of FIG. 14.

Turning now to FIGS. 17 and 18, another embodiment of a wax warmer 600 is depicted. The wax warmer 600 includes a lower housing portion 112, a reservoir 106, an electrical cord 138, and the sealed heater engine 200" of FIG. 14. The wax warmer 600 also includes a heater engine mounting base 602 that is configured to retain the sealed heater engine 200" in thermal contact with the reservoir 106. The wax warmer 600 may also include a silicone spacer 164 positioned between the heater engine mounting base 602 and the sealed heater engine 200" to limit heat transfer away from the reservoir 106 and into the lower housing portion 112. Further, an insulating or mica pad 604 may be positioned between the sealed heater engine 200" and the reservoir 106.

Figure 19:
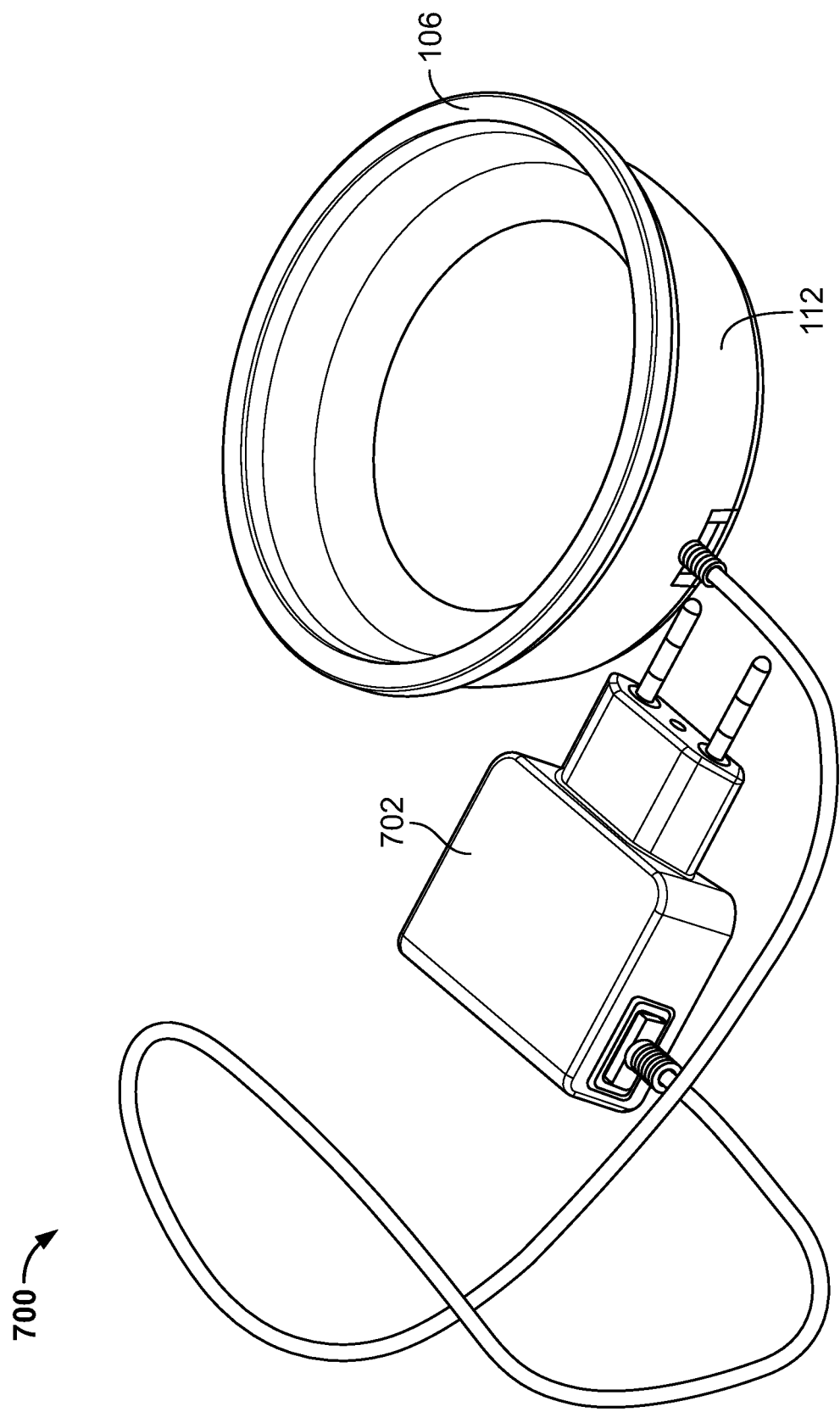
FIG. 19 is an isometric view of a top, rear, and side of the electric wax warmer of FIG. 17 and configured with a DC power supply.
Figure 20:
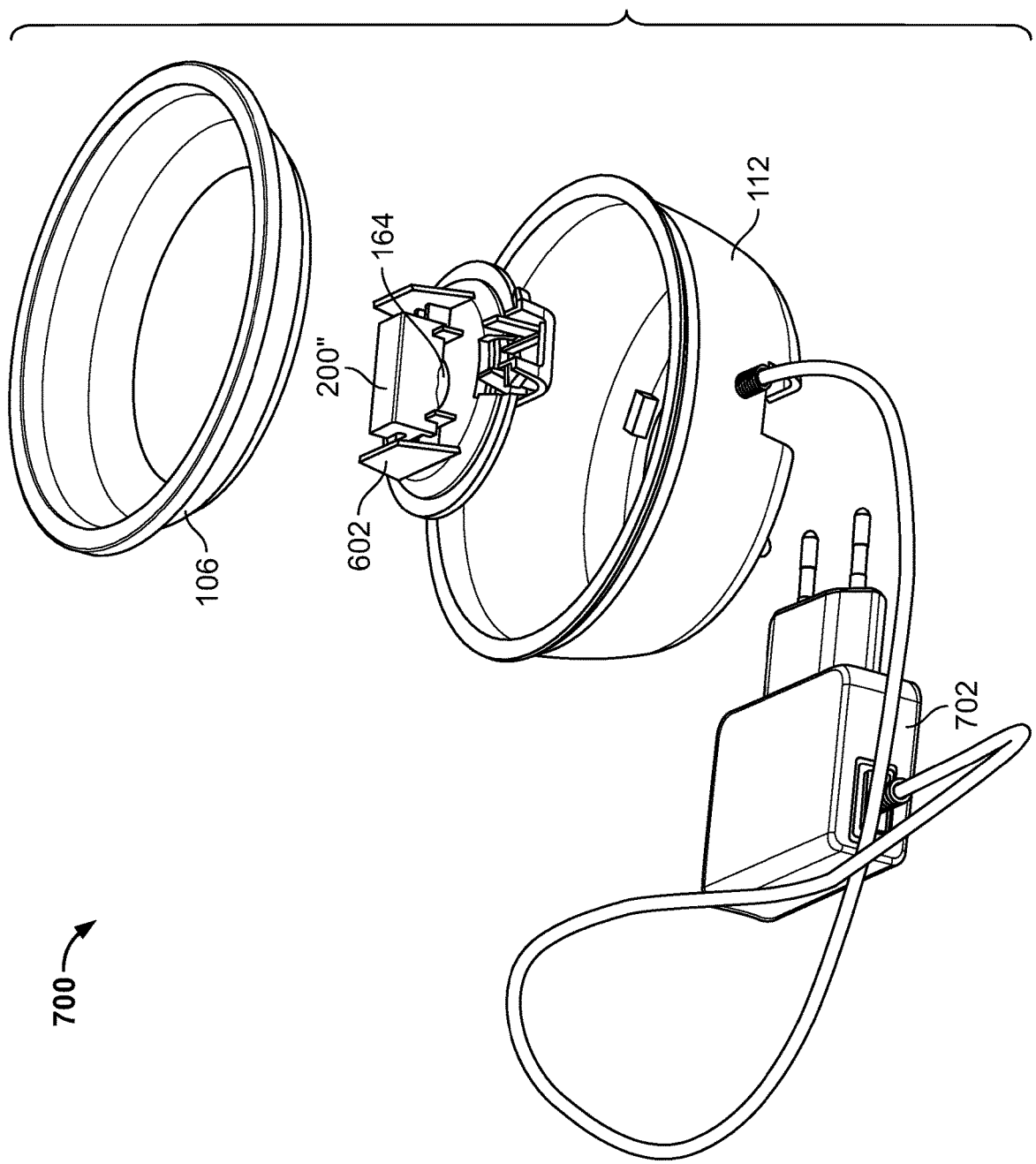
FIG. 20 is an exploded, isometric view of the electric wax warmer of FIG. 19 having the sealed heater engine of FIG. 14 and configured with a DC power supply.

Turning now to FIGS. 19 and 20, another embodiment of a wax warmer 700 is depicted. The wax warmer 700 includes all of the same components as the wax warmer 600, except that the standard electrical cord 138 has been replace with a DC transformer 702, which provides a low voltage output.

It is contemplated that the embodiments of wax warmers provided within the present specification are water resistant and the sealed heater engines 200 are hermetically sealed. These properties provide a significant degree of safety when the wax warmers are used in environments where they may be accidentally exposed to water or other liquids. By sealing the wax warmer housing and the heater engines it is possible to produce a wax warmer that significantly reduces the risk of electric shock to a user when the wax warmer is accidentally exposed to water or other liquids.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmer that utilizes wax melts or the like.

INDUSTRIAL APPLICABILITY

A wax warmer is presented that provides a sealed heater engine. Thus, a user may be protected from an electrical shock in the event that the wax warmer accidentally contacts or is exposed to water.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A warmer, comprising:
a reservoir for receiving a melt, the reservoir defining uninterrupted bottom and side walls;
a housing defining an interior volume and configured to receive the reservoir, wherein the housing includes an upper portion and a lower portion, and wherein the upper portion is retained securely on the lower portion by a plurality of retention tubes; and
a sealed heater engine comprising a second housing with a heater disposed therein, and positioned within the interior volume, the second housing being in thermal contact with the reservoir, wherein the sealed heater engine includes a seal having an ultrasonically welded portion that prevents the ingress of liquids into the sealed heater engine.

2. The warmer of claim 1, wherein the second housing of the sealed heater engine comprises a top cover and a base, and wherein a combination of an o-ring seal, a wire seal, the top cover, and the base results in the sealed heater engine exceeding the water resistant standards of UL 283.

3. The warmer of claim 2, wherein the upper portion and the lower portion are sealed to prevent the ingress of water, and a seal is formed between the upper portion and the lower portion that includes an ultrasonically welded portion.

4. The warmer of claim 3, wherein the sealed heater engine includes the o-ring positioned between the top cover and the base.

5. The warmer of claim 4, wherein the sealed heater engine further includes the top cover and the base joined by the ultrasonically welded portion.

6. The warmer of claim 1, wherein the sealed heater engine includes the heater encapsulated in thermal potting material.

7. The warmer of claim 6, wherein the sealed heater engine further includes a sealed pass through for an electrical connection.

8. The warmer of claim 3, wherein the reservoir includes a channel configured to couple to the upper portion of the housing.

9. The warmer of claim 8, wherein the channel of the reservoir forms a water resistant seal when coupled to the upper portion of the housing.

10. A warmer, comprising:
a reservoir for receiving a melt;
a housing including an upper portion and a lower portion that define an interior volume, wherein the upper portion is configured to receive the reservoir and the reservoir is positioned within the interior volume; and
electrical components comprising at least a sealed heater engine comprising a second housing with a heater disposed therein and positioned within the interior volume, the second housing being in thermal contact with the reservoir,
wherein the sealed heater engine includes a seal having an ultrasonically welded portion to prevent liquids from reaching an interior of the sealed heater engine, and
wherein the electrical components are disposed entirely below a bottommost wall of the reservoir.

11. The warmer of claim 10, wherein the second housing of the sealed heater engine comprises a top cover and a base, and wherein the seal includes at least an o-ring positioned between the top cover and the base and a pass through seal.

12. The warmer of claim 11, wherein the ultrasonically welded portion of the seal joins the top cover to the base.

13. The warmer of claim 12, wherein the seal allows the warmer to meet or exceed the water resistant standards of UL 283.

14. A warmer, comprising:
a reservoir for receiving a melt, the reservoir defining uninterrupted bottom and side walls;
a housing defining an interior volume and configured to receive the reservoir, wherein the housing includes an upper portion and a lower portion, and wherein the upper portion includes a plurality of retention cylinders that cooperate with a plurality of retention tubes in the lower portion to secure the upper portion to the lower portion;

a power cord;

a sealed heater engine comprising a second housing with a heater disposed therein, and positioned within the interior volume, the second housing being in thermal contact with the reservoir, wherein the sealed heater engine includes a seal having an ultrasonically welded portion that prevents the ingress of liquids into the sealed heater engine; and wherein the housing defines an opening to receive the power cord.

15. The warmer of claim 14, wherein the upper portion and the lower portion that are sealed to prevent the ingress of water, and a seal is formed between the upper portion and the lower portion that includes an ultrasonically welded portion.

16. The warmer of claim 14, wherein the second housing of the sealed heater engine comprises a top cover and a base, and wherein the sealed heater engine includes at least an o-ring positioned between the top cover and the base.

17. The warmer of claim 16, wherein the sealed heater engine further includes the top cover and the base joined by the ultrasonically welded portion.

18. The warmer of claim 14, wherein the sealed heater engine includes the heater encapsulated in thermal potting material.

19. The warmer of claim 17, wherein the sealed heater engine further includes a sealed pass through for an electrical connection.

20. The warmer of claim 19, wherein the sealed heater engine formed by the o-ring, the top cover, the base, and the sealed pass through exceeds the water resistant standards of UL 283.

* * * * *